United States Patent
Kim et al.

(10) Patent No.: US 10,517,963 B2
(45) Date of Patent: Dec. 31, 2019

(54) GENE DELIVERY SYSTEM USING POLYMER NETWORK

(71) Applicants: INSTITUTE FOR BASIC SCIENCE, Daejeon (KR); POSTECH ACADEMY-INDUSTRY FOUNDATION, Gyeongsangbuk-do (KR)

(72) Inventors: Won Jong Kim, Gyeongsangbuk-do (KR); Jinhwan Kim, Gyeongsangbuk-do (KR)

(73) Assignees: Institute for Basic Science, Daejeon (KR); POSTECH ACADEMY-INDUSTRY FOUNDATION, Gyeongsangbuk-do (KR)

( * ) Notice: Subject to any disclaimer, the term of this patent is extended or adjusted under 35 U.S.C. 154(b) by 0 days.

(21) Appl. No.: 15/337,252

(22) Filed: Oct. 28, 2016

(65) Prior Publication Data

US 2017/0274098 A1    Sep. 28, 2017

(30) Foreign Application Priority Data

Mar. 25, 2016 (KR) .................. 10-2016-0035848

(51) Int. Cl.
| | | |
|---|---|---|
| *A61K 48/00* | (2006.01) | |
| *C08G 73/02* | (2006.01) | |
| *C08B 37/08* | (2006.01) | |
| *C08G 69/10* | (2006.01) | |

(52) U.S. Cl.
CPC ........ *A61K 48/0041* (2013.01); *C08B 37/003* (2013.01); *C08G 69/10* (2013.01); *C08G 73/0206* (2013.01)

(58) Field of Classification Search
USPC ................................ 424/450, 489
See application file for complete search history.

(56) References Cited

FOREIGN PATENT DOCUMENTS

| KR | 100466254 B1 | 1/2005 | |
|---|---|---|---|
| WO | WO-2010019718 A2 * | 2/2010 | ........... A61K 9/5146 |

OTHER PUBLICATIONS

Ji et al., ACS Appl. Mater. Interfaces 2016, 8, 9565-9576 (Year: 2016).*
Kim, J., "Phenylboronic Acid-Sugar Grafted Polymer Architecture as Tumor Targetable and Dual-Stimuli Responsive Gene Carrier," Summary of Oral Proceedings of the 115th General Meeting of the Korean Chemical Society, Apr. 15, 2015, South Korea, 1 page.
Kim, J. et al., "Phenylboronic acid-sugar grafted polymer architecture as a dual stimuli-responsive gene carrier for targeted anti-angiogenic tumor therapy," Biomaterials, vol. 75, Jan. 2016, Available Online Oct. 14, 2015, 10 pages.
Otsuka, H. et al., "Anomalous Binding Profile of Phenylboronic Acid with N-Acetylneuraminic Acid (Neu5Ac) in Agueous Solution with Varying pH," Journal of the American Chemical Society, vol. 125, No. 12, Oct. 2002, 10 pages.
Weiss, S. et al., "Uronic acids functionalized polyethyleneimine (PEI)- polyethyleneglycol (PEG)-graft-copolymers as novel synthetic gene carriers," Biomaterials, vol. 27, No. 10, Apr. 2006, Published Online Dec. 6, 2005, 11 pages.
Ji, M. et al., "Sialic Acid-Targeted Nanovectors with Phenylboronic Acid-Grafted Polyethylenimine Robustly Enhance siRNA-Based Cancer Therapy," ACS Applied Materials and Interfaces, vol. 8, No. 15, Apr. 20, 2016, Published Online Mar. 23, 2016, 12 pages.

* cited by examiner

*Primary Examiner* — Janet L Epps-Smith
(74) *Attorney, Agent, or Firm* — McCoy Russell LLP

(57) ABSTRACT

Provided is a gene delivery including a polymer network formed by binding phenylboronic acid, sugar, and a low-molecular weight branched polymer. The gene delivery may be stably maintained in vivo and efficiently deliver a gene specifically to cancer cells, such that the gene delivery system may be usefully used as a gene delivery system for chemotherapy.

6 Claims, 15 Drawing Sheets

US 10,517,963 B2

GENE DELIVERY SYSTEM USING POLYMER NETWORK

CROSS-REFERENCE TO RELATED APPLICATIONS

This application claims priority under 35 U.S.C. § 119 to Korean Patent Application No. 10-2016-0035848, filed on Mar. 25, 2016, in the Korean Intellectual Property Office. The disclosure of which is incorporated herein by reference in its entirety for all purposes.

TECHNICAL FIELD

The following disclosure relates to a technology for delivering a gene in a cell through a gene delivery including a polymer network formed by phenylboronic acid, a polymer, and sugar.

BACKGROUND

Gene therapy is a next generation therapeutic technology expected to treat various diseases, but a suitable carrier, or the like, for effectively delivering a gene has not yet been sufficiently developed.

Recently, research into carriers using external or internal stimulation has been actively conducted, and these stimulation-responsive carriers are expected to be introduced into cells and released from endosome in the cells to thereby effectively deliver a material or drug for gene therapy to a target position. For example, there is a technology of effectively delivering a gene or drug from a carrier containing the gene or drug to a target position by internal stimulation through an acidic environment, a reduction condition, or the like, in cells.

A gene delivery micelle containing a hydrophilic polymer capable of delivering a gene by an acidic condition in cells has been disclosed in Korean Patent No. 0466254.

Various technologies for introducing a gene, a drug, or the like, into cells have been developed, but the development of a delivery system for efficiently and accurately delivering a gene delivery material such as a nucleic acid to a target position in cells has been still required.

RELATED ART DOCUMENT

Patent Document (Patent Document 1) Korean Patent No. 0466254

SUMMARY

An embodiment of the present invention is directed to providing a gene delivery capable of effectively delivering a gene to a target position in cells through the gene delivery in which a polymer network containing phenylboronic acid is formed, particularly, a gene delivery capable of effectively delivering a gene specifically to cancer cells.

In one general aspect, a gene delivery includes a polymer network formed by binding phenylboronic acid, sugar, and a low-molecular weight branched polymer.

In another general aspect, a gene delivery system includes a polymer network formed by binding phenylboronic acid, sugar, and a low-molecular weight branched polymer, and delivers a gene by an acidic condition and a change in ATP concentration in cells.

DETAILED DESCRIPTION OF EMBODIMENTS

Figure 1A:
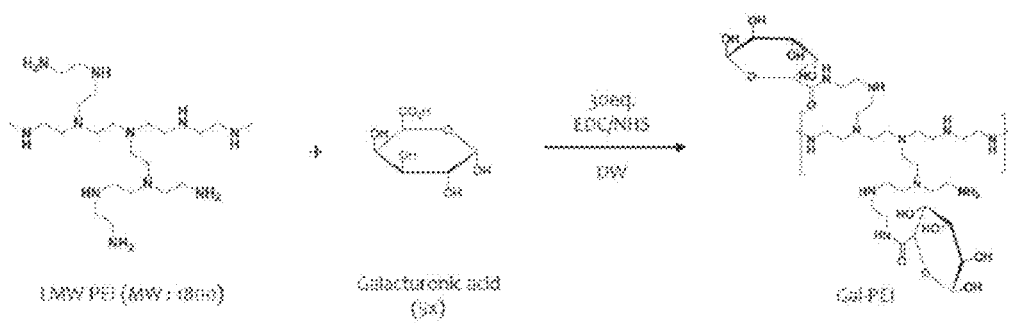
FIGS. 1A and 1B illustrate a method of preparing 3-fluoro-4-carboxyphenylboronic acid (PBA)-bound polyethyleneimine (PEI) (PBA-PEI) and galacturonic acid-bound PEI (Gal-PEI).

The present invention will be described in detail. Unless indicated otherwise in the specification, all terms used herein should be construed as meaning as those that are generally used in the art, and the drawings may be exaggerated, or portions thereof obscuring the gist of the present invention may be omitted.

The present invention provides a gene delivery including a polymer network formed by binding phenylboronic acid, sugar, and a low-molecular weight branched polymer. Phenylboronic acid may selectively bind with cis-diol in sugar, thereby making it possible to form a polymer network organized through a polymer capable of binding to phenylboronic acid and sugar.

In detail, a low-molecular weight branched polymer to which phenylboronic acid is bound and a low-molecular weight branched polymer to which sugar is bound are prepared, respectively, and then, mixed with each other, such that the branched polymers are cross-linked by phenylboronic acid and sugar, thereby forming the polymer network. That is, in the polymer network according to the present invention, phenylboronic acid and sugar are bound to polymers, respectively, to form single constituent units, and a multiple bond between these constituent units are induced, thereby constituting an organized polymer network.

According to an exemplary embodiment of the present invention, the low-molecular weight branched polymers are bound to phenylboronic acid and sugar via amide bonds, respectively, and the phenylboronic acid bound to the low-molecular weight branched polymer and the sugar bound to the low-molecular weight branched polymer are bound to each other, thereby making it possible to form the polymer network.

According to the present invention, phenylboronic acid and sugar may be selectively bound to each other by cis-diols of phenylboronic acid and sugar, and phenylboronic acid and sugar bound to each other may be easily dissociated from each other in acidic environment or an environment in which a different kind of sugar is present at a high concentration, such that binding and dissociation may be adjusted by a change in sugar concentration. The acidic environment or the environment in which a different kind of sugar is present at a high concentration may be formed in cells, thereby making it possible to provide a gene delivery through intracellular stimulation using binding characteristics of phenylboronic acid and sugar. That is, the gene delivery according to the present invention, including the polymer network may deliver a gene depending on the intracellular stimulation as an intercellular stimulation-responsive gene delivery.

According to the present invention, since phenylboronic acid may specifically bind to N-acetylneuraminic acid and N-acetylneuraminic acid is particularly over-expressed in cancer cell surfaces, the gene delivery according to the present invention, including the polymer network using phenylboronic acid may specifically recognize and bind to cancer cells. The gene delivery according to the present invention may respond to intracellular stimulation to deliver a gene to cancer cells by specific cancer recognition of phenylboronic acid and selective binding and dissociation of phenylboronic acid and sugar. The specific gene delivery as described above may be effectively used to treat cancer through gene therapy.

According to the exemplary embodiment of the present invention, in the case of using a gene delivery including a polymer network in which phenylboronic acid is additionally conjugated with the PEGylated polymer network in vivo, gene delivery may be more stably maintained in vivo, and tumor targeting characteristics may be more excellent.

According to the exemplary embodiment in the present invention, high-concentration sugar in cells may correspond to adenosine triphosphate (ATP), and gene delivery efficiency may be decreased by inhibiting ATP stimulation.

In the present invention, a polymer for forming the polymer network may be preferably a cationic polymer, but is not limited thereto. For example, the polymer network may be formed using polyethyleneimine, polyacrylamide, polymethylacrylamide, poly-L-lysine, or chitosan as the cationic polymer.

In the present invention, it is preferable that the polymer for forming the polymer network is a branched polymer having a low molecular weight. A molecular weight of the low-molecular weight branched polymer may be 600 Da to 3,000 Da, 1,200 Da to 2,000 Da, 1,700 Da to 1,900 Da and preferably, 1,500 Da to 2,000 Da, but is not limited thereto. A low-molecular weight branched cationic polymer may allow the gene delivery to rarely cause cytotoxicity in cells and may increase gene delivery efficiency several times to several ten times.

According to the exemplary embodiment of the present invention, the low-molecular weight branched polymer may form amide bonds with phenylboronic acid and sugar, respectively, to thereby be conjugated therewith. It is preferable that the low-molecular weight branched polymer is conjugated with phenylboronic acid and sugar via the amide bonds, respectively, but is not limited thereto. The kind of bonds may be changed depending on the kind of polymer or sugar.

In the present invention, sugar may be one or more selected from the group consisting of glucose, fructose, galactose, ribose, and mannose, but is not limited thereto.

In the present invention, the acidic condition at which selective binding between phenylboronic acid and sugar may be dissociated may be pH 6.0 or less, preferably, pH 4.5 to 5.5, but is not limited thereto.

In the present invention, in the case in which stimulation of high-concentration sugar in cells is ATP stimulation, when an ATP concentration may be 3 mM or more, 5 mM or more, preferably, 3 to 5 mM, and more preferably, 4.5 to 5.5 mM, the selective binding between phenylboronic acid and sugar may be dissociated from each other, but the present invention is not limited thereto.

According to the exemplary embodiment of the present invention, gene delivery efficiency of the gene delivery including the polymer network may be changed by stimulation caused by the acidic environment and a change in ATP concentration. In the case in which the acidic environment is formed and ATP concentration is increased, gene delivery efficiency may be remarkably increased by two different kinds of stimulation, but gene may be efficiently delivered by any one of the acidic environment and the change in ATP concentration.

In the gene delivery according to the present invention, the polymer network and genes electrostatically interact with the cationic polymer to thereby be stabilized, and phenylboronic acid is specifically bound to N-acetylneuraminic acid in cell surfaces, such that the gene delivery may be introduced into cells by a mechanism such as endocytosis, or the like.

The gene delivery introduced into cells may respond to stimulation by the acidic environment or a high-concentration sugar environment in the cells to thereby deliver genes. For example, in the gene delivery delivered in cells by endocytosis, phenylboronic acid and sugar bound to the polymer network are dissociated by an acidic environment in endosome. Thereafter, the polymer network in which dissociation occurs due to destruction of endosome is moved to cytoplasm, and dissociation is further promoted by high-concentration ATP in cytoplasm, thereby delivering genes. In this case, since phenylboronic acid may be bound to N-acetylneuraminic acid expressed in cancer cell surfaces, the gene delivery may specifically deliver genes particularly to cancer cells.

A method of preparing a gene delivery according to the present invention may include: preparing a phenylboronic acid-bound low-molecular weight branched polymer and a sugar-bound low-molecular weight branched polymer; mixing the phenylboronic acid-bound low-molecular weight branched polymer and the sugar-bound low-molecular weight branched polymer with each other under a basic condition to form a polymer network; and removing a low-molecular weight compound to perform purification.

According to the present invention, a method of preparing a gene delivery, which is suitable for being used in vivo, may further include: PEGylating after forming the polymer network; and additionally conjugating phenylboronic acid therewith.

Hereinafter, exemplary embodiments of the present invention will be described in more detail through Examples. The following Examples are only examples, and the present invention is not limited thereby.

Figure 1B:
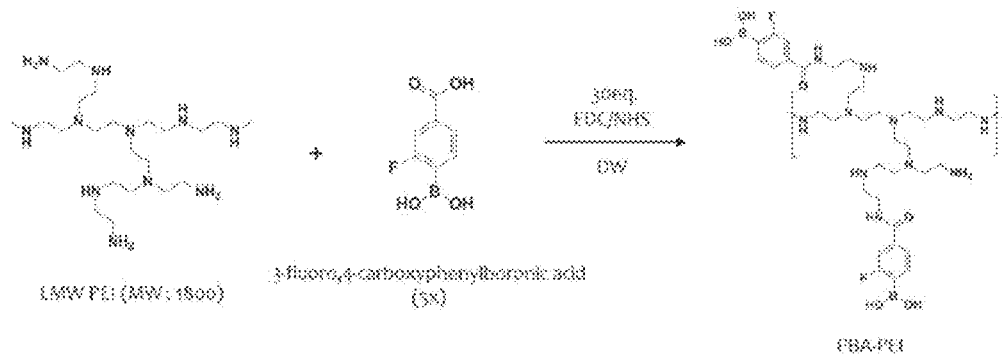
Figure 2:
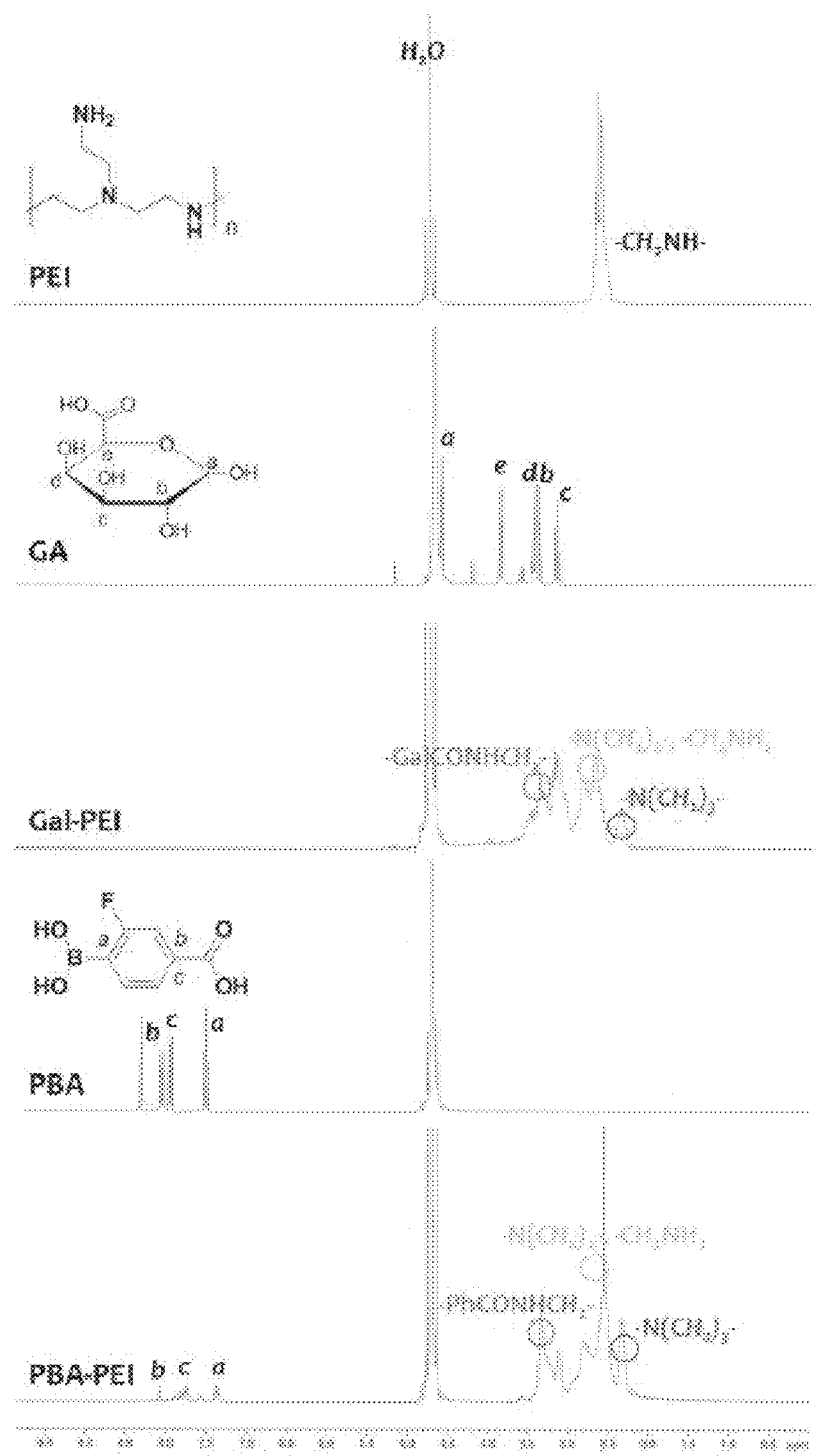
FIG. 2 illustrates proton nuclear magnetic resonance ($^1$H-NMR) results of PBA-bound PEI (PBA-PEI) and galacturonic acid-bound PEI (Gal-PEI).
Figure 3:
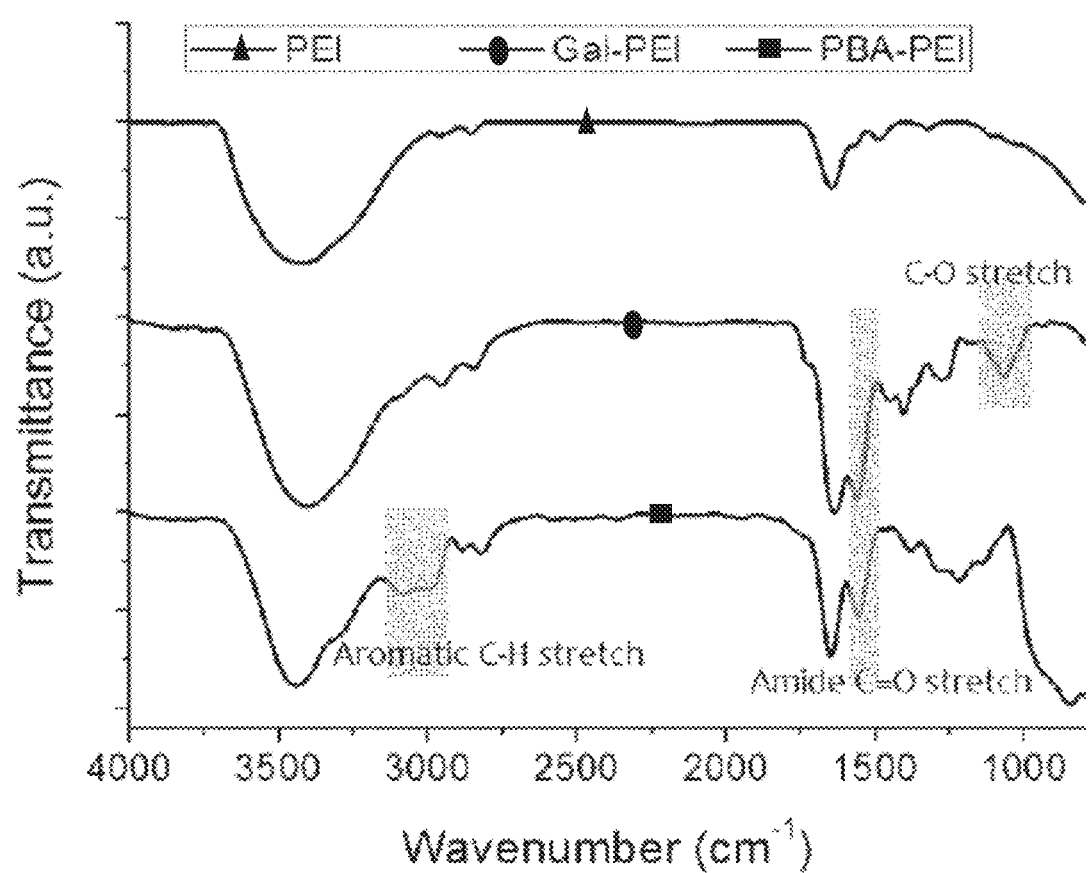
FIG. 3 illustrates Fourier transform infrared spectroscopy (FT-IR) results of PBA-bound PEI (PBA-PEI) and galacturonic acid-bound PEI (Gal-PEI).
Figure 4A:
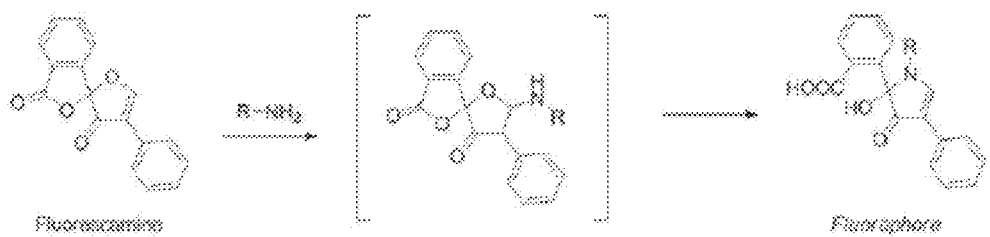
FIG. 4A illustrates a fluorescamine assay method of PBA-bound PEI (PBA-PEI) and galacturonic acid-bound PEI (Gal-PEI) and FIG. 4B illustrates fluorescamine assay results thereof.
Figure 4B:
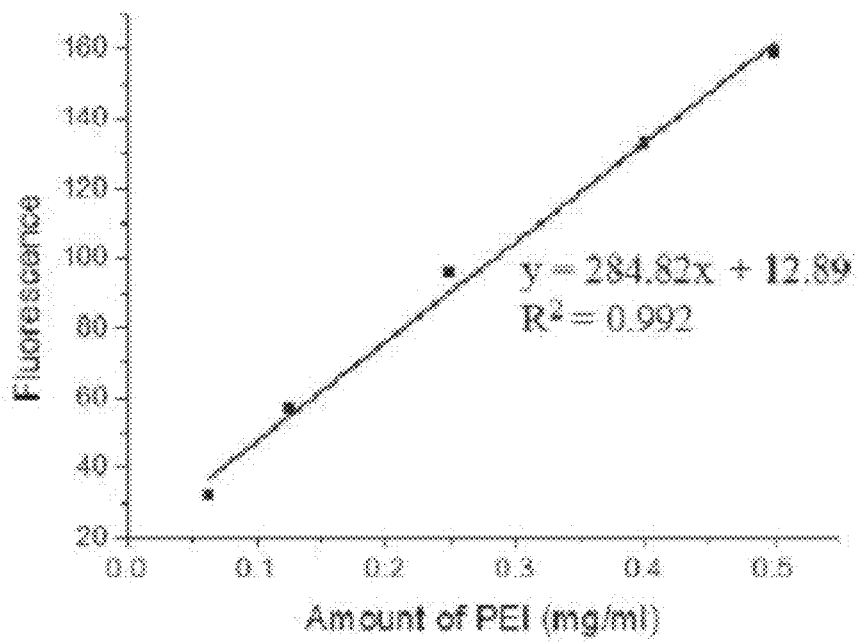
Figure 5:
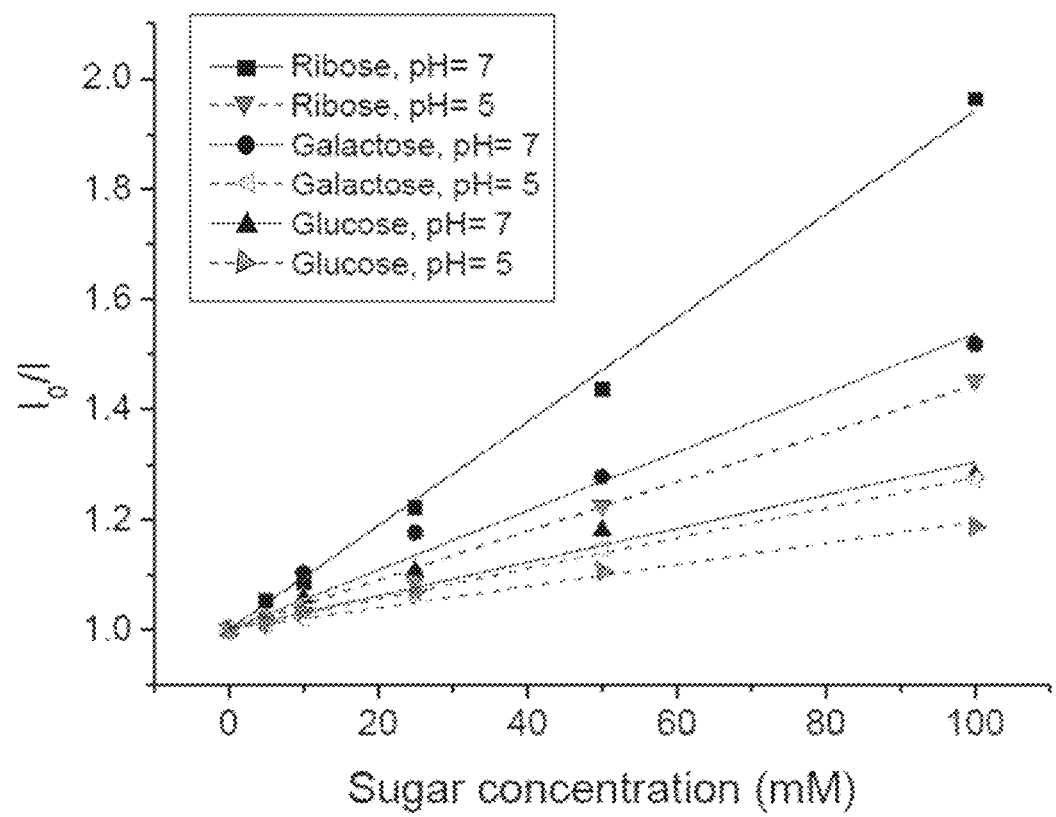
FIG. 5 illustrates a binding degree between sugar and PBA through steady-state fluorescence quenching assay.

Example 1. Preparation of Polymer Network 1-1. Synthesis of Phenylboronic Acid or Galacturonic Acid-Conjugated Polyethyleneimine Branched polyethyleneimine (PEI) corresponding to a cationic polymer, galacturonic acid (GA) for conjugating sugar, and 3-fluoro-4-carboxyphenylboronic acid (PBA) for conjugating phenylboronic acid were prepared. PEI (100 mg, 1.8 kDa) was dissolved in deionized water and pH was adjusted to 7.4. After galacturonic acid (5 equivalents) and PBA (5 equivalents) were dissolved in deionized water, respectively, 1-ethyl-3-(3-(dimethylamino)propyl) carbodiimide hydrochloride (EDC, 30 equivalents) and N-hydroxysuccinimide (NHS) were dissolved while being stirred. After 30 minutes, the PEI solution was added dropwise to the galacturonic acid solution and the PBA solution, respectively, and reacted overnight. After reactions, unreacted materials were removed from each of the solutions by dialysis with water using a cellulose membrane dialysis bag (MWCO=1,000 Da) for 2 days, thereby obtaining PBA-bound PEI (PBA-PEI) and galacturonic acid-bound PEI (Gal-PEI) (FIGS. 1A and 1B). $^1$H-NMR and Fourier Transform Infrared (FT-IR) spectra show that PEI was successfully bound to sugar and PBA (FIGS. 2 and 3). PBA-bound PEI (PBA-PEI) and galacturonic acid-bound PEI (Gal-PEI) were confirmed by back titration from an amount of primary amines through fluorescamine assay (FIGS. 4A and 4B). Binding between sugar and PBA was confirmed using steady-state fluorescence quenching assay (FIG. 5).

Figure 6:
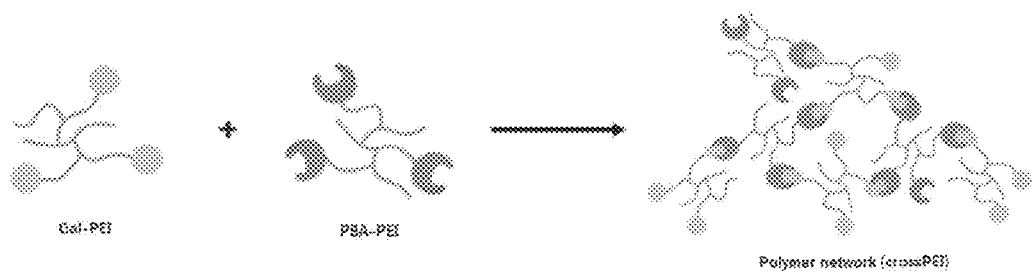
FIG. 6 illustrates a polymer network (CrossPEI) formed by mixing PBA-bound PEI (PBA-PEI) and galacturonic acid-bound PEI (Gal-PEI).
Figure 7:
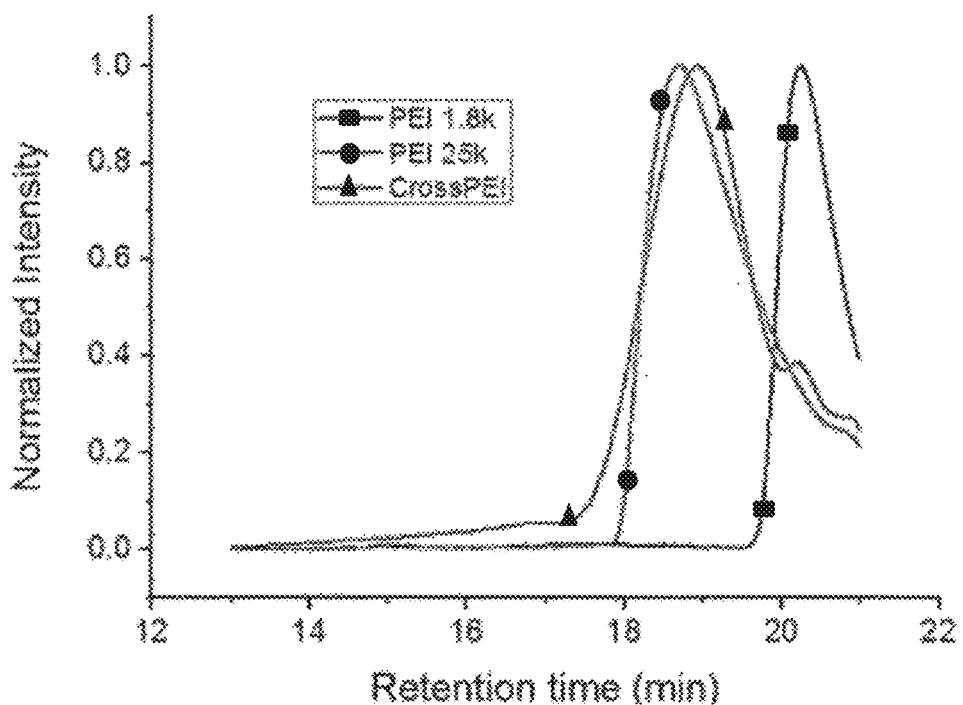
FIG. 7 illustrates a molecular weight of the polymer network through gel-permeation chromatography.
Figure 8:
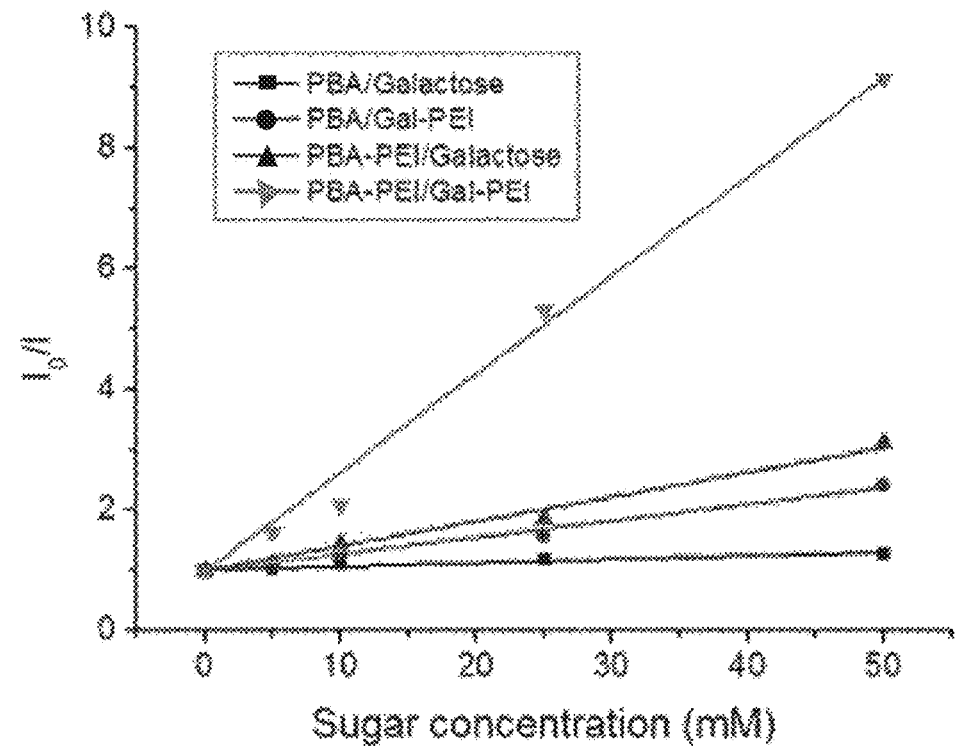
FIG. 8 illustrates stability of a polymer network formed using phenylboronic acid, sugar, and a low-molecular weight branched polymer.

1-2. Preparation of Polymer Network by Binding of Phenylboronic Acid, Sugar, and Branched Polyethyleneimine A Gal-PEI solution (10 mg/mL) and a PBA-PEI solution (10 mg/ml) were mixed and reacted with each other while stirring overnight. Membrane centrifugation (MWCO=3000 Da, 4000 rpm) was performed on reaction solution for 20 minutes in a tris-acetate buffer (pH 8.2, containing 0.3 M NaCl) five times to purify the reaction solution, thereby forming a polymer network (CrossPEI) (FIG. 6). A molecular weight of the polymer network was confirmed through gel permeation chromatography (GPC), and the polymer network was detected between polyethyleneimine (1.8 kDa) and polyethyleneimine (25 kDa), such that it was confirmed that a low-molecular weight polymer network was formed (FIG. 7). An amount of cross-linked polyethyleneimine was confirmed using copper acetate (CuOAc) amine quantification assay. The polymer network formed by binding between Gal-PEI and PBA-PEI was stable enough to have a Ka value equal to or more than 30 times Ka values in a case in which a polymer network was formed by a multiple bond between a diol residue of galactose and PBA and a case in which there was no PBA or galactose or cross-linking by PEI was not formed (FIG. 8).

1-3. Confirmation of Cytotoxicity

Figure 9:
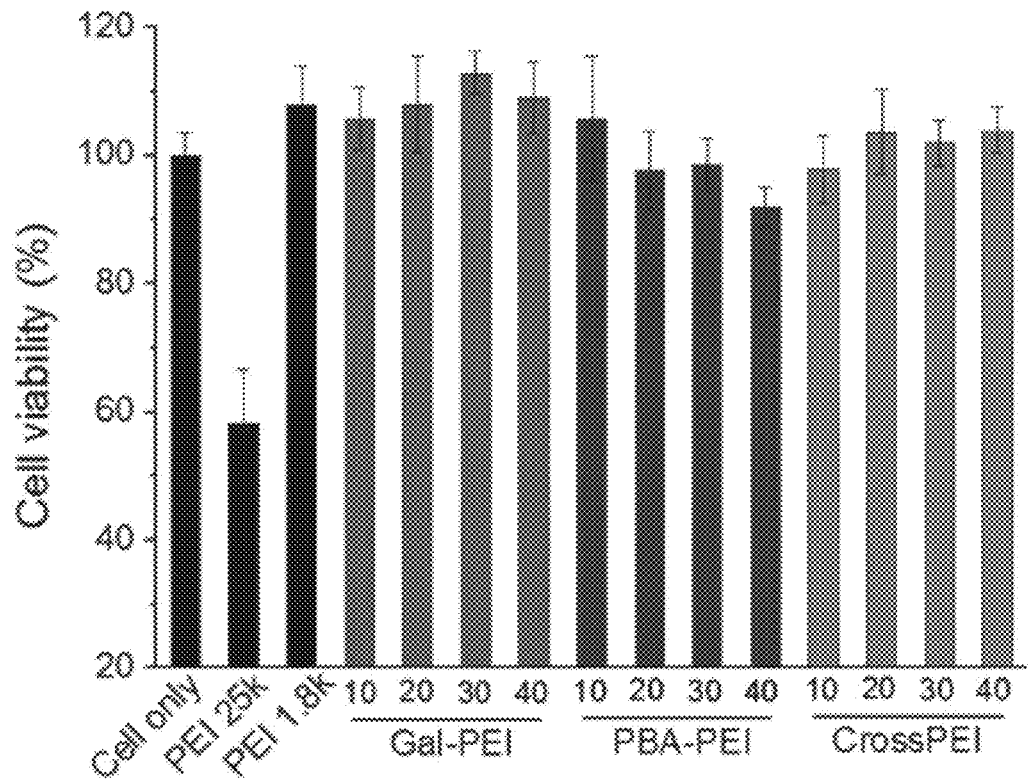
FIG. 9 illustrates cytotoxicity results of PBA-bound PEI (PBA-PEI), galacturonic acid-bound PEI (Gal-PEI), and the polymer network (CrossPEI) through 3-(4,5-dimethylthiazol-2-yl)-2,5-diphenyltetrazolium bromide (MTT) assay.

In order to confirm cytotoxicity, MCF-7 cells (human breast adenocarcinoma cell line) and PC-3 cells (human prostate cancer cell line) were prepared by culturing in a RPMI-1640 (Roswell Park Memorial Institute, Hyclone) medium, and HeLa (human uterine cervical cancer cell line) was prepared by culturing in a Dulbecco's modified Eagle's medium (DMEM, Hyclone) medium. Each of the cells was treated with a polymer network (CrossPEI) containing DNA (0.2 μg/well), and in order to confirm cytotoxicity, MTT assay was performed. As a result of performing the MTT assay, cytotoxicity of the polymer network itself was not exhibited, and since the polymer network was decomposed into low-molecular weight branched PEI (1.8 kDa), Gal-PEI, and PBA-PEI, which have low toxicity, while releasing DNA, cytotoxicity was rarely exhibited (FIG. 9).

Figure 10:
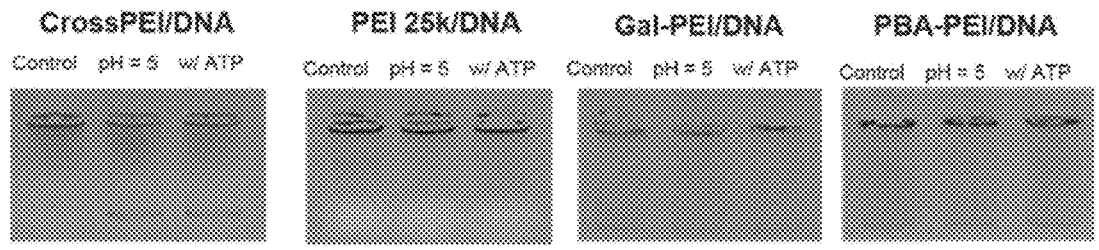
FIG. 10 illustrates agarose gel electrophoresis results of polyplexes in which a high-molecular weight PEI (25 kDa), PBA-bound PEI (PBA-PEI), galacturonic acid-bound PEI (Gal-PEI), and the polymer network (CrossPEI) are bound to DNAs, respectively, depending on an acidic condition (pH 5) and adenosine triphosphate (ATP) concentration.
Figure 11A:
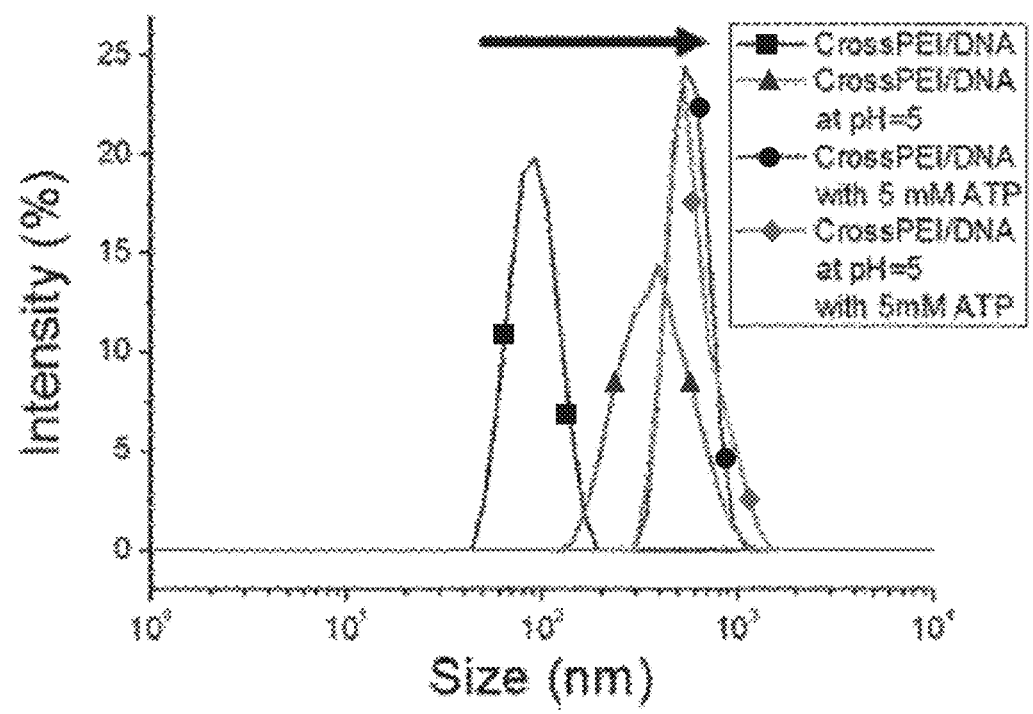
FIG. 11A illustrates a result obtained by measuring a hydrodynamic volume of the polyplex in which the polymer network (CrossPEI) is bound to DNA depending on changes in pH and ATP concentration.
Figure 11B:
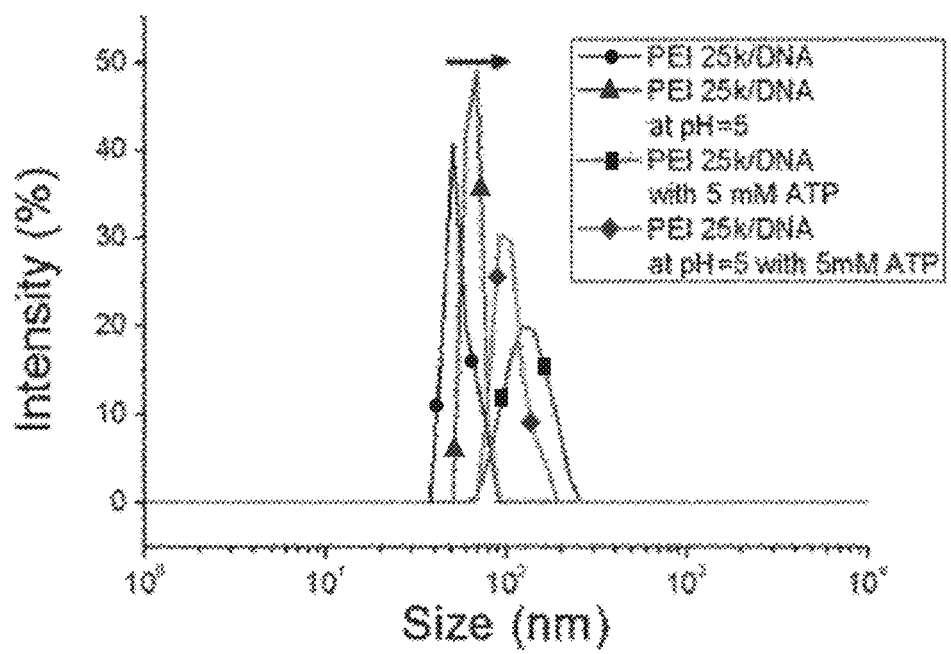
FIG. 11B illustrates a result obtained by measuring a hydrodynamic volume of the polyplex in which high-molecular weight PEI (25 kDa) is bound to DNA depending on pH and ATP concentration.

Example 2. Confirmation of Release Efficiency of DNA Bound to Polymer Network by Stimulation It was confirmed through gel retardation assay at various N/P ratios that PBA-bound PEI (PBA-PEI), galacturonic acid-bound PEI (Gal-PEI) and the polymer network (CrossPEI) were bound to DNAs, respectively. CrossPEI had a high charge density to thereby be strongly bound to DNA as compared to Gal-PEI or PBA-PEI, and was decomposed into Gal-PEI or PBA-PEI by stimulation such as a low pH concentration and a high ATP concentration, thereby promoting DNA release. This phenomenon may be confirmed through 1% agarose gel electrophoresis after incubating a polyplex of PEI cross-linked with DNA under an acidic pH condition or 5 mM ATP condition (FIG. 10 to FIG. 11B). In a case in which Gal-PEI, PBA-PEI, or PEI (25 kDa) was bound to DNA, DNA was rarely released by an acidic pH or ATP concentration stimulation in cells, and it was confirmed by an acidic pH or high ATP concentration in the cells that DNA was effectively released from the polymer network.

Example 3. Confirmation of Gene Delivery by Polymer Network

Figure 12:
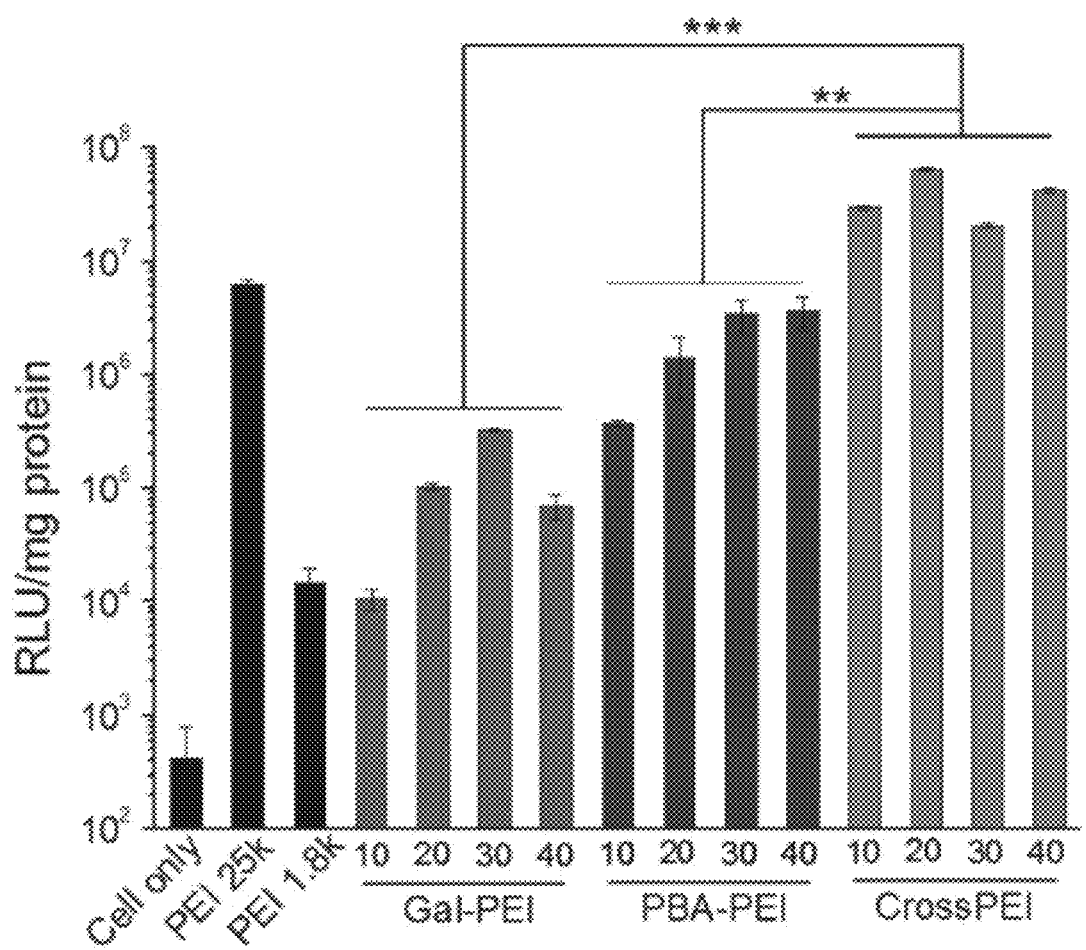
FIG. 12 illustrates degrees of gene delivery by PBA-bound PEI (PBA-PEI), galacturonic acid-bound PEI (Gal-PEI), and the polymer network (CrossPEI).
Figure 13:
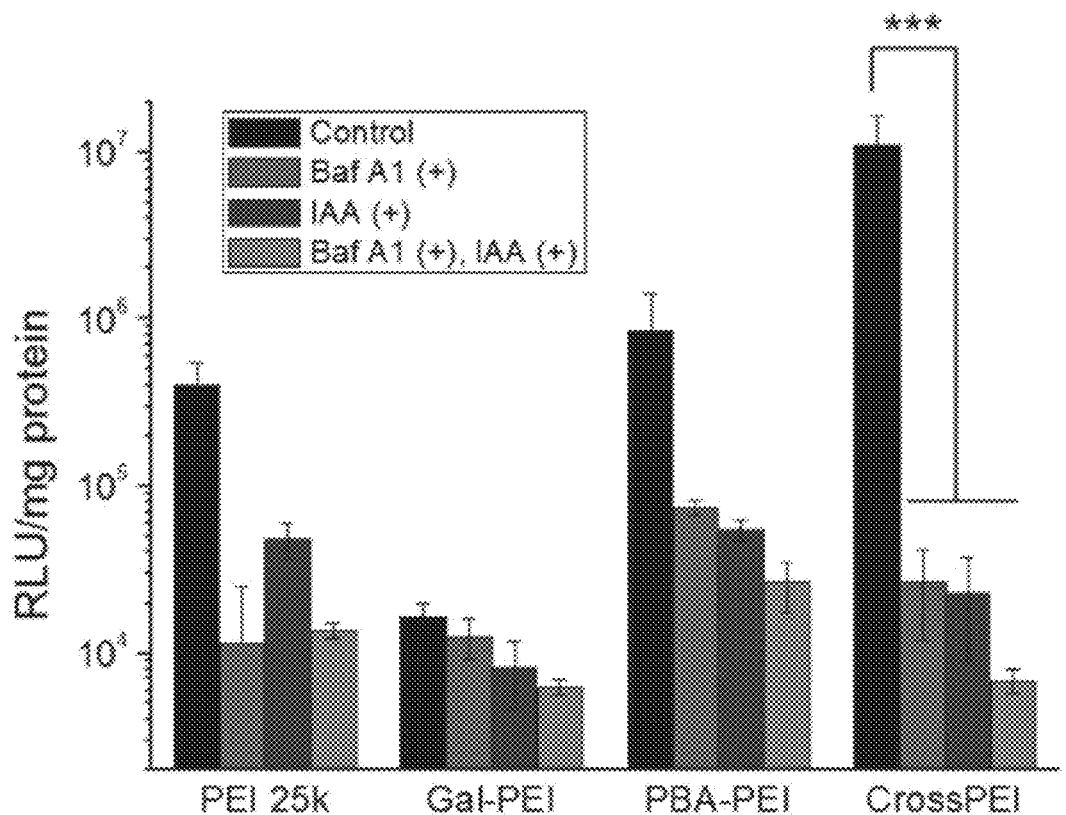
FIG. 13 illustrates degrees of gene delivery by PEI (25 kDa), PBA-PEI, Gal-PEI, and CrossPEI at the time of treating cells with bafilomycin (Baf) A1 and iodoacetic acid (IAA).

In order to evaluate gene transfection by the polymer network, luciferasegene reporter assay was performed in MCF-7, HeLa, and PC-3 cells. Each of the cells were seeded in a 24-well culture plate at a density of $3 \times 10^4$ cells/well and cultured for 1 day under the same condition. Different polyplexes containing DNAs were prepared by adding DNA (1 μg/well) to PEI (25 kDa), PEI (1.8 kDa), Gal-PEI, PBA-PEI, and the polymer network (CrossPEI), respectively, at various N/P ratios, and a final volume of these polyplexes was 20 μl. After each of the cells was cultured in 200 μl of a serum-free medium containing the polyplex for 2 hours, the medium was replaced with 500 μl of a medium containing 9% serum, followed by culturing for 22 hours. Thereafter, the cells were washed with Dulbecco's phosphate buffered saline (DPBS) buffer and dissolved by lysis buffer. Expression of luciferasegene reporter was measured using a microplate spectrofluorimeter (VICTOR 3 VMulti-label Counter, PerkinElmer, Wellesley, Mass.). Transfection efficiency was low in PEI (1.8 k) and Gal-PEI due to low charge density, and gene transfection efficiency in PBA-PEI was higher than that in PEI (1.8 k). As compared to PBA-PEI and Gal-PEI, the polymer network had a high gene transfection effect in all cell lines (FIG. 12). It was confirmed that the reason of this effect was that the polymer network formed by cross-linking PBA-PEI and Gal-PEI may form a dense polyplex including DNA due to a high charge density, and the polymer network may efficiently release the DNA while being decomposed by the stimulation caused by the acidic pH and ATP concentration in the cells. Additionally, in order to specifically confirm a gene delivery mechanism of the polyplex, MCF-7 cells were pre-treated with bafilomycin A1 to suppress acidification of endosome during endocytosis of the polyplex, and in order to suppress formation of ATP in cells, the MCF-7 cells were pre-treated with iodoacetic acid as an ATP blocker. Thereafter, gene transfection results were confirmed (FIG. 13). As a result, it was confirmed that the gene delivery mechanism was caused by the acidic environment and a change in ATP concentration in the cells.

Example 4. Confirmation of Gene Delivery Using Gene Delivery Including Polymer Network After additionally conjugating polyethylene glycol to the polymer network in order to confirm a cancer cell-specific gene, a gene delivery including a polymer network in which phenylboronic acid is conjugated with a terminal of the polyethylene glycol-conjugated polymer network was prepared. In detail, 6-arm polyethylene glycol succinimidyl succinate (6-arm PEG-SS) was mixed with the polymer network for PEGylation so that an amine ratio of succinidyl succinate and PEI was 1:5, thereby obtaining a PEG-conjugated polymer network (PEG-CrossPEI). In order to conjugate PBA with the PEG-conjugated polymer network, 3-aminophenylboronic acid (3 equivalents) was added thereto. Then, membrane centrifugation (MWCO=10 kDa, 4000 rpm) was performed for 20 minutes five times, thereby obtaining a gene delivery (PBA-PEG-CrossPEI) including the polymer network as a finally purified product.

Figure 14:
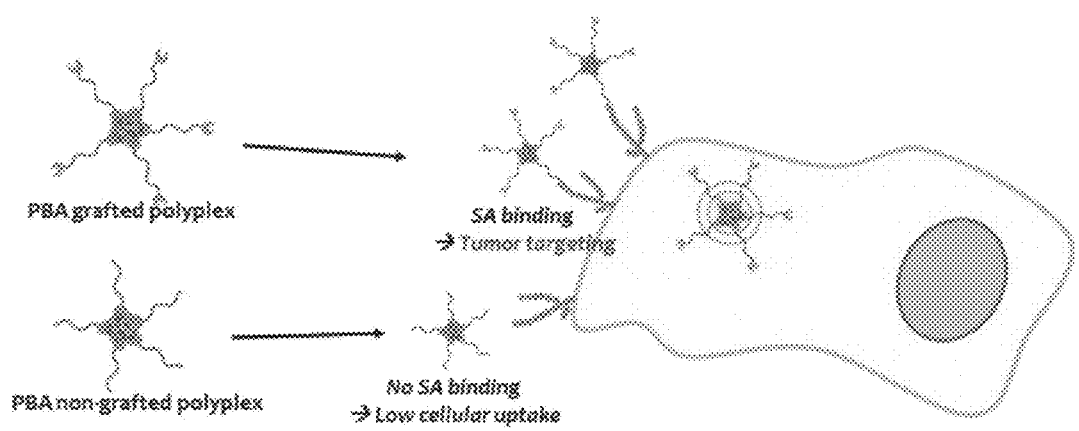
FIG. 14 illustrates tumor targeting by PBA exposed to a surface in a PBA-PEG-CrossPEI/DNA polyplex.
Figure 15:
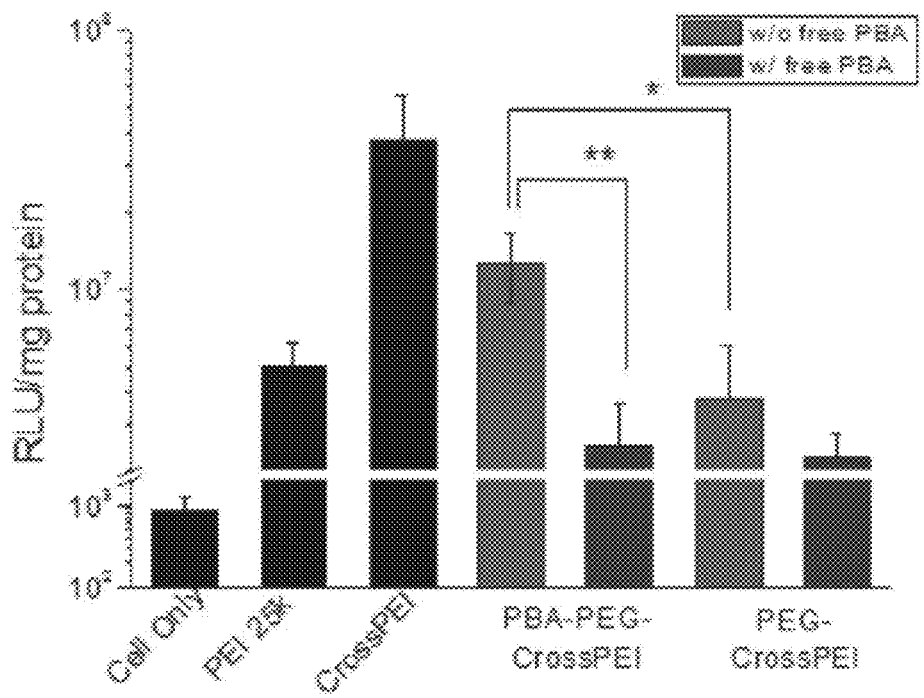
FIG. 15 illustrates degrees of gene delivery in vivo by a PEGylated polymer network (PEG-CrossPEI) and a polymer network (PBA-PEG-CrossPEI) in which phenylboronic acid is conjugated by PEGylation.
Figure 16:
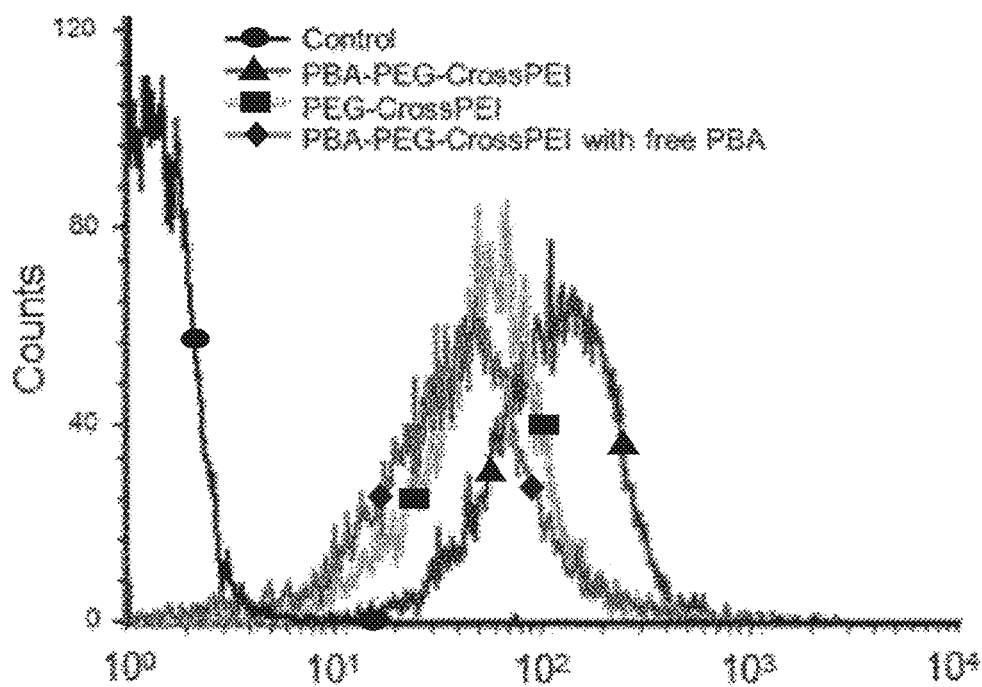
FIG. 16 illustrates results of measuring degrees of introduction of respective polyplexes into cells through flow cytometry analysis in the case of treating the cells with a PEGylated polymer network (PEG-CrossPEI), treating the cells with a polymer network (PBA-PEG-CrossPEI) in which phenylboronic acid is conjugated by PEGylation, and treating the cells simultaneously with the polymer network (PBA-PEG-CrossPEI) in which phenylboronic acid is conjugated by PEGylation and PBA.
Figure 17:
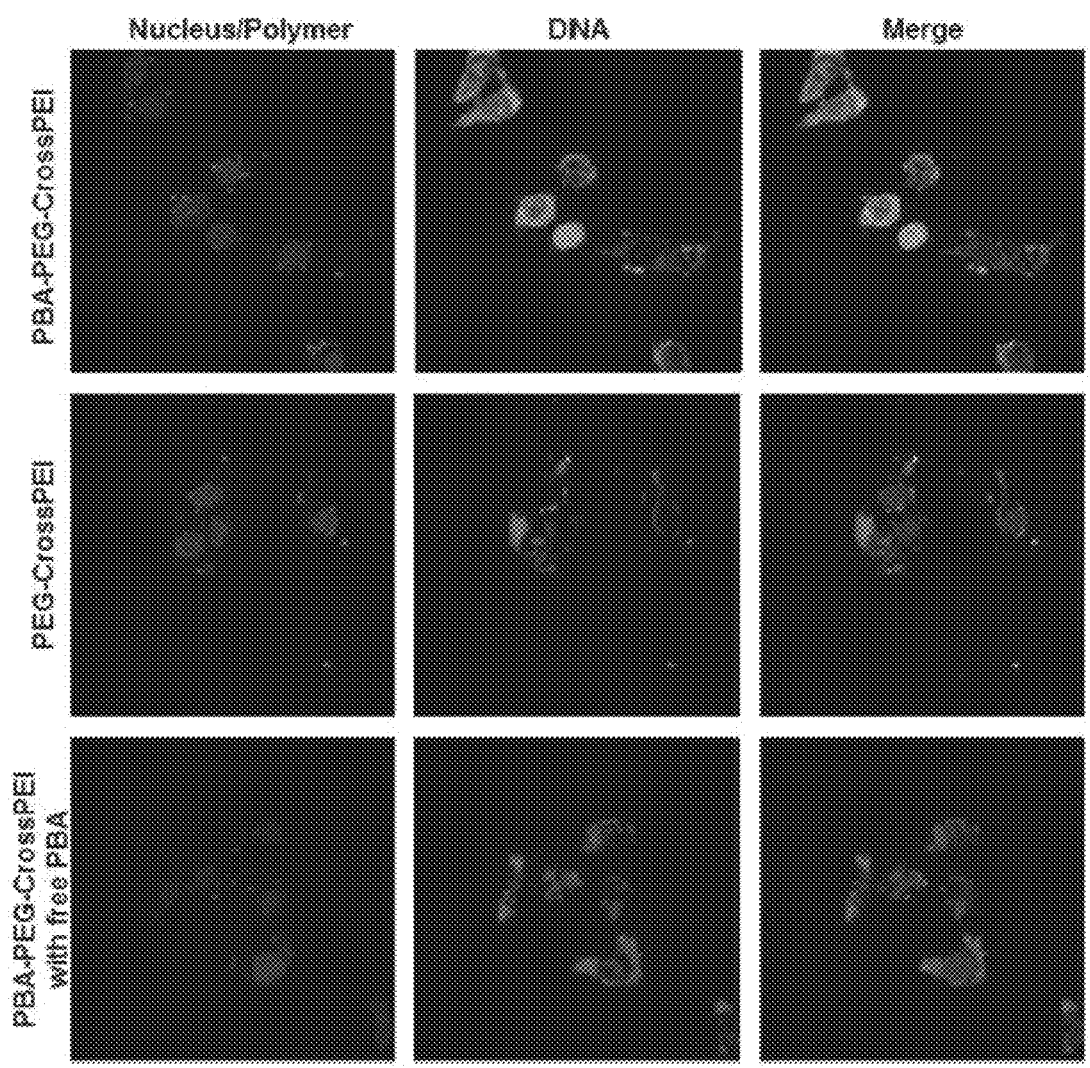
FIG. 17 illustrates results of observing degrees of introduction of respective polyplexes into cells through confocal scanning laser microscopy in the cases of treating the cells with a PEGylated polymer network (PEG-CrossPEI), treating the cells with a polymer network (PBA-PEG-CrossPEI) in which phenylboronic acid is conjugated by PEGylation, and treating the cells simultaneously with the polymer network (PBA-PEG-CrossPEI) in which phenylboronic acid is conjugated by PEGylation and PBA.

PBA-PEG-CrossPEI/DNA corresponding to a polyplex in which PBA-PEG-CrossPEI and DNA were bound to each other was prepared. The PBA-PEG-CrossPEI/DNA polyplex was stably maintained at a 5 mM glucose concentration corresponding to a glucose level in the blood, and in the PBA-PEG-CrossPEI/DNA polyplex, PBA was exposed to a surface of the polyplex to serve as a targeting moiety (FIG. 14). It was confirmed through the luciferasegene reporter assay that in vitro, gene transfection efficiency of the PBA-PEG-CrossPEI/DNA polyplex was higher than that of using PEI (25 k) and lower than that in the case of using only the polymer network (CrossPEI) alone. However, in vivo, the PEGylated polymer network was maintained in the blood for a long period of time and a targeting function thereof was more excellent, as compared to the case of using only the polymer network. In addition, gene transfection efficiency of PBA-PEG-CrossPEI was three times higher than that of PEG-CrossPEI (FIG. 15). In order to confirm endocytosis of the polyplex, PBA-PEG-CrossPEI/DNA and PEG-CrossPEI/DNA labeled with FNR-648 were prepared, and MCF-7 cells were treated with the FNR-648-labeled PBA-PEG-CrossPEI/DNA and PEG-CrossPEI/DNA and cultured in serum-free RPMI. Thereafter, an introduction amount of the polyplex into the cells was confirmed through flow cytometry analysis using FACS Calibur (Becton Dickinson and BD Cell Quest software (Becton Dickinson) (FIG. 16). It was confirmed that in the case of using PBA-PEG-CrossPEI, the PBA-PEG-CrossPEI was more efficiently introduced into the cells as compared to PEG-CrossPEI. The reason is that PBA forms strong binding with a cell membrane. Further, in the case of pre-treating only PBA, introduction efficiency into the cells was decreased. Therefore, it was confirmed that a PBA moiety in PBA-PEG-CrossPEI adjusted introduction of the PBA-PEG-CrossPEI into the cells. Finally, a degree of introduction of a polymer including PBA into cells was confirmed through confocal laser scanning microscopy. First, MCF-7 cells were seeded in a 12-well culture plate at a density of $3 \times 10^4$ cells/well and cultured for 1 day. Next, each of the wells was treated with PBA-PEG-CrossPEI and PEG-CrossPEI polyplexes including 1 μg of DNA and cultured in serum-free RPMI for 2 hours. After adding cool DPBS thereto to perform endocytosis, the cells were washed and fixed using 4% paraformaldehyde for 1 day. After fixation, the cells were treated with a mounting medium containing DAPI so that the cells were mounted on a cover slide, and the cells were observed by confocal scanning laser microscopy (FIG. 17). In the case of gene transfection by PBA-PEG-CrossPEI, a stronger and more uniform fluorescent signal was observed as compared to the case of treating the cells with PEG-CrossPEI and the case of pre-treating the cells with PBA and treating the pre-treated cells with PBA-PEG-CrossPEI.

Example 5. Confirmation of Tumor Targeting In Vivo

In order to confirm tumor targeting in vivo, mice (MCF-xenograft mice) with a tumor formed by grafting MCF-7 cells were used. After preparing three groups each including three randomly selected mice, normal saline, a PBA-PEG-CrossPEI/DNA polyplex and a PEG-CrossPEI/DNA polyplex were intravenously injected thereinto, respectively.

Figure 18:
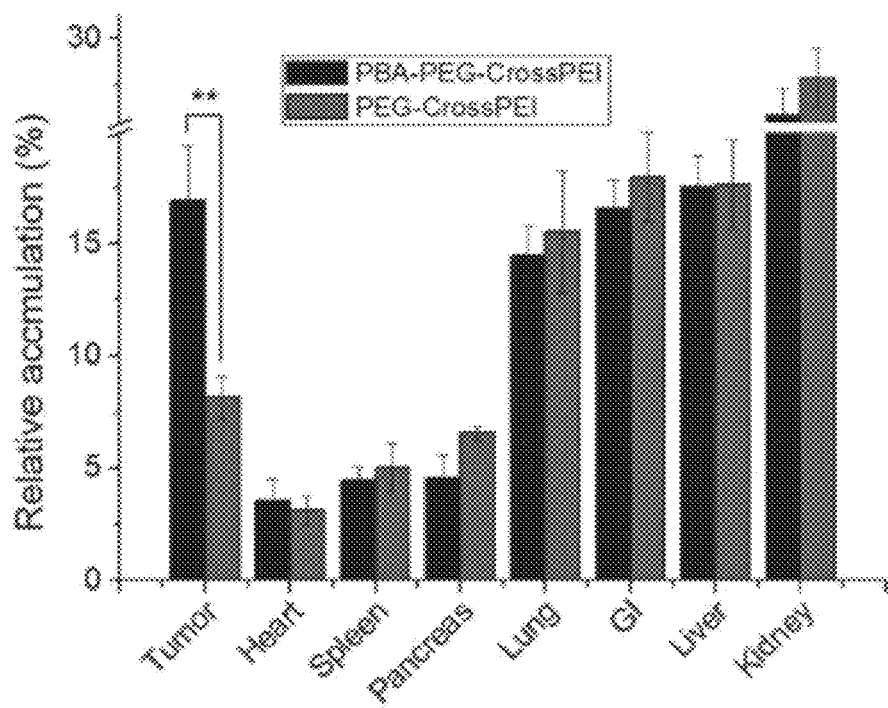
FIG. 18 illustrates degrees of tumor targeting in vivo by a PEGylated polymer network (PEG-CrossPEI) and a polymer network (PBA-PEG-CrossPEI) in which phenylboronic acid is conjugated by PEGylation.

After 6 hours, the mice were euthanized, and fluorescence of each organ was confirmed and analyzed using IVIS Spectrum (Caliper Lifesciences, Hopkinston, Mass.) (FIG. 18). As a result of analysis, an accumulation amount of the PBA-PEG-CrossPEI/DNA polyplex was two times higher than that of the PEG-CrossPEI/DNA polyplex in tumor. Therefore, it was confirmed that a polyplex modified with PBA may effectively target tumor. Even though another material capable of binding to the PBA moiety such as glucose was present in vivo unlike in vitro, binding affinity of another material capable of binding to the PBA moiety was decreased by an acidic condition in a tumor portion, such that the PBA-PEG-CrossPEI/DNA polyplex may be selectively bound to and internalized into tumor cells.

Example 6. Confirmation of Chemotherapeutic Effect In Vivo

Figure 19:
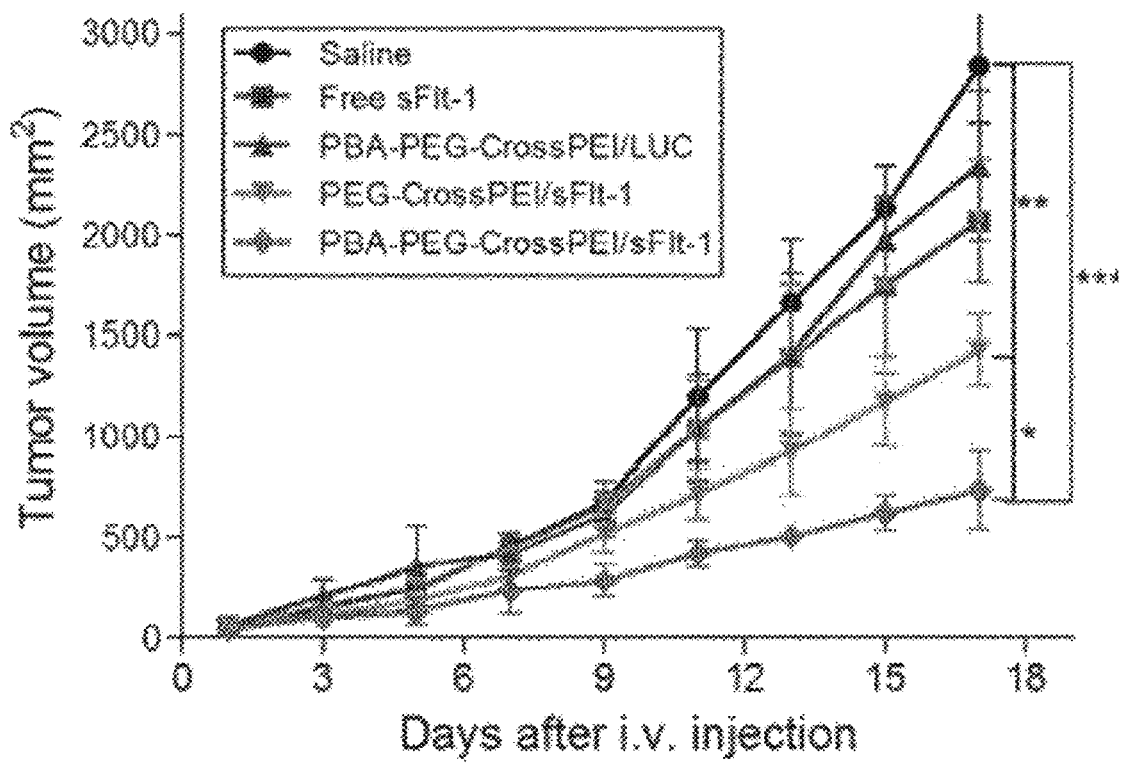
FIG. 19 illustrates tumor proliferation suppression in vivo by a polymer network (PBA-PEG-CrossPEI) in which phenylboronic acid is conjugated by PEGylation.
Figure 20:
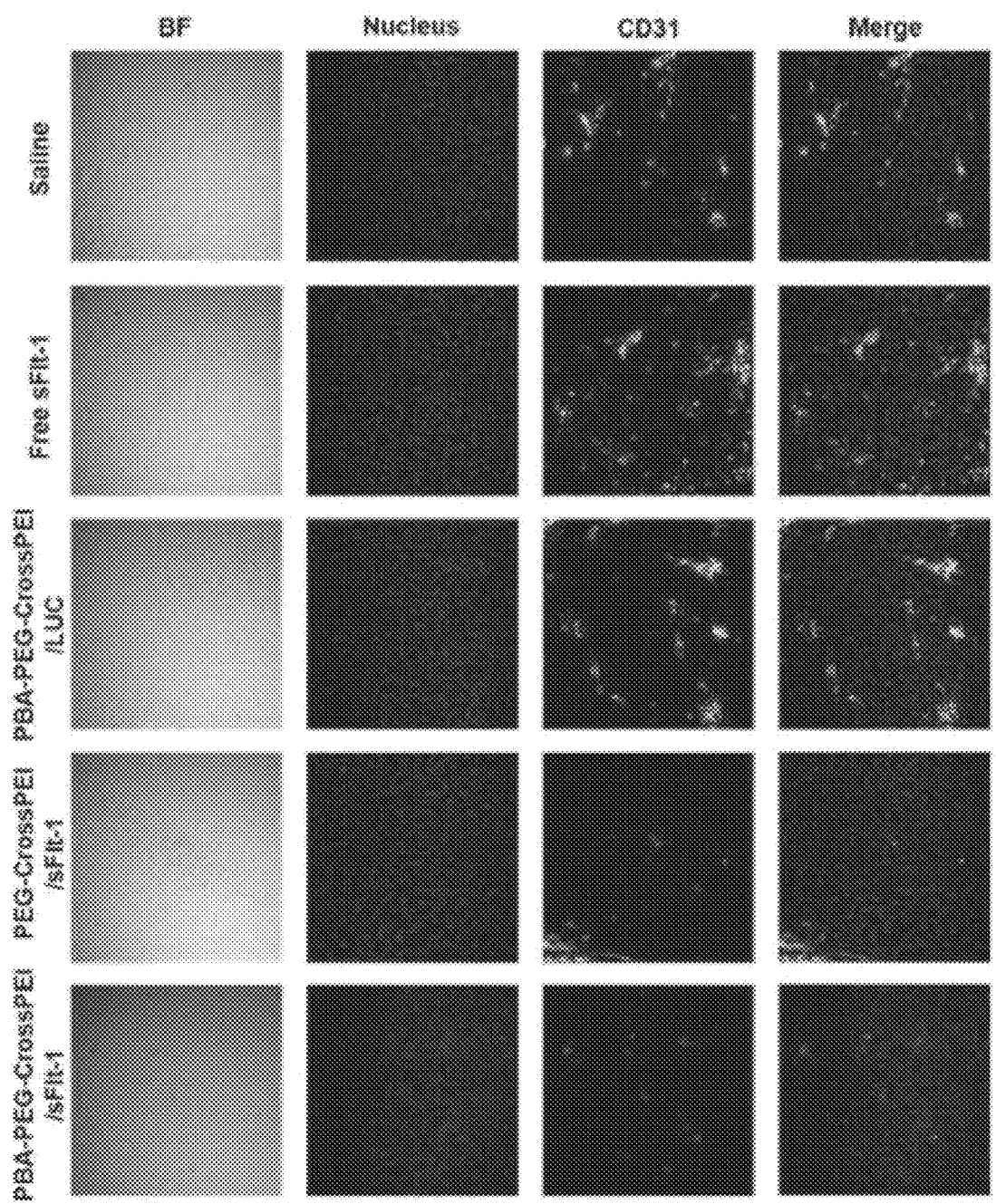
FIG. 20 illustrates tumor-specific delivery results of an anti-angiogenic gene vector in vivo by a polymer network (PBA-PEG-CrossPEI) in which phenylboronic acid is conjugated by PEGylation.
Figure 21:
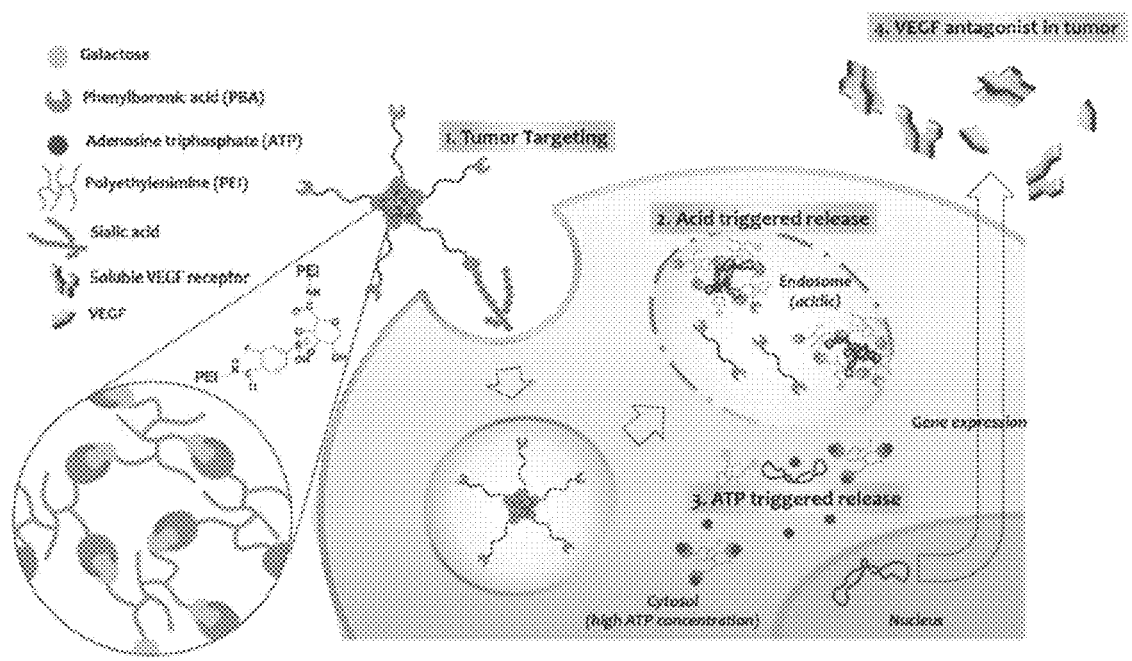
FIG. 21 illustrates a configuration of a gene delivery including a polymer network in which phenylboronic acid is conjugated by PEGylation and a gene delivery system in vivo.

In order to confirm a chemotherapeutic effect in vivo, mice in which tumor was formed by grafting CT-26 cells and sFlt-1 pDNA coding a water soluble portion of a VEGF receptor for suppressing angiogenesis were used. After preparing five groups each including five randomly selected mice, normal saline, sFlt-1 pDNA, a PBA-PEG-CrossPEI/sFlt-1 pDNA polyplex, a PBA-PEG-CrossPEI/LUC pDNA polyplex, and a PEG-CrossPEI/sFlt-1 pDNA polyplex were intravenously injected every 7 days, respectively, so that 40 μg of DNA was injected into each mouse. A change in tumor size was measured every 2 days using an electronic caliper (FIG. 19). It was confirmed that in the mice into which the PBA-PEG-CrossPEI/sFlt-1 pDNA polyplex and the PEG-CrossPEI/sFlt-1 pDNA polyplex were injected, the tumor was slowly proliferated from seven days, but in other mice, the tumor was rapidly proliferated. Further, in order to analyze tumor tissue through immunohistochemical staining, tumor tissue was collected from the mice in each of the groups, fixed by paraffin, treated with a CD31 antibody, and treated with FITC-labeled anti-goat antibody as a secondary antibody, and then, the resultant was confirmed by confocal scanning electron microscopy (FIG. 20). In the mouse group into which the PBA-PEG-CrossPEI/sFlt-1 pDNA polyplex was injected, a CD31 staining intensity was weak, but other mouse groups, the CD31 staining intensity was strong. It was confirmed from the result as described above that an anti-angiogenesis gene vector was delivered by tumor-specific targeting and may be applied as a delivery for treating cancer.

The gene delivery according to the present invention may effectively deliver a gene by allowing a process of introducing the gene into cells, releasing the gene to the cytoplasm in the cells, and delivering the gene to various target positions including the nucleus in the cells to be performed by intercellular stimulation or an environmental change. Due to this feature, the gene delivery may be used in gene therapy for safely and efficiently delivering genes and treating various diseases, and used to deliver various materials to be introduced into cells, such as a drug, and the like, as well as the gene.

The invention claimed is:

1. A gene delivery system comprising a polymer network formed by binding a first polyethyleneimine to phenylboronic acid via amide bonds and a second polyethyleneimine to sugar via amide bonds, and binding the phenylboronic acid bound to the first polyethyleneimine and the sugar bound to the second polyethyleneimine to each other by the phenylboronic acid and a cis-diol of the sugar to form boronate ester binding.

2. The gene delivery system of claim 1, wherein phenylboronic acid binds to N-acetylneuraminic acid when it is exposed to N-acetylneuraminic acid over-expressed and exposed on a surface of a cancer cell.

3. The gene delivery system of claim 1, wherein the sugar is selected from the group consisting of glucose, fructose, galactose, and mannose.

4. The gene delivery system of claim 1, wherein the first and second polyethyleneimines have a molecular weight of 1.2 kDa to 2.0 kDa.

5. The gene delivery system of claim 1, wherein the binding between the phenylboronic acid and the sugar dissociates at a pH of 4.5 to 5.5.

6. The gene delivery system of claim 1, wherein the binding between the phenylboronic acid and the sugar dissociates when an ATP concentration of a target cell is 3 mM or more.

* * * * *